United States Patent [19]

Cosentino et al.

[11] Patent Number: 5,578,267

[45] Date of Patent: *Nov. 26, 1996

[54] CYLINDRICAL BLOOD HEATER/OXYGENATOR

[75] Inventors: Louis C. Cosentino; Jeffrey A. Lee, both of Plymouth; Daniel A. Baker, Minnetonka, all of Minn.

[73] Assignee: Minntech Corporation, Minneapolis, Minn.

[*] Notice: The term of this patent shall not extend beyond the expiration date of Pat. No. 5,270,004.

[21] Appl. No.: 511,287

[22] Filed: Aug. 4, 1995

Related U.S. Application Data

[60] Continuation of Ser. No. 263,817, Jun. 22, 1994, abandoned, which is a division of Ser. No. 115,996, Sep. 2, 1993, abandoned, which is a continuation of Ser. No. 844,620, May 11, 1992, Pat. No. 5,270,004.

[51] Int. Cl.⁶ ........................................ A61M 1/14
[52] U.S. Cl. .................. 422/46; 422/48; 261/DIG. 28; 210/321.64; 210/321.79; 210/321.88
[58] Field of Search ............... 422/46, 48; 261/DIG. 28; 210/321.64, 321.79, 321.88

[56] References Cited

U.S. PATENT DOCUMENTS

| | | | |
|---|---|---|---|
| 1,248,898 | 12/1917 | Parks | 242/159 |
| 1,357,434 | 11/1920 | Anderson | 242/159 |
| 1,482,909 | 2/1924 | Calkins | 242/159 |
| 2,259,364 | 10/1941 | Bartholomew | 242/159 |
| 2,539,942 | 1/1951 | Beeftink | 242/159 |
| 2,605,053 | 7/1952 | Broden | 242/26 |
| 2,652,831 | 9/1953 | Chesler | 128/214 |
| 2,934,067 | 4/1960 | Calvin | 128/214 |
| 3,204,631 | 9/1965 | Fields | 128/214 |
| 3,291,568 | 12/1966 | Sautter | 422/44 |
| 3,332,746 | 7/1967 | Claff et al. | 422/44 |
| 3,339,341 | 9/1967 | Maxwell et al. | 55/16 |
| 3,396,849 | 8/1968 | Lande et al. | 210/321 |
| 3,422,008 | 1/1969 | McLain | 210/22 |
| 3,468,631 | 9/1969 | Raible et al. | 422/44 |
| 3,480,401 | 11/1969 | Holm et al. | 422/44 |
| 3,489,647 | 1/1970 | Kolobow | 195/1.8 |
| 3,579,810 | 5/1971 | Mon et al. | 29/527.1 |
| 3,768,977 | 10/1973 | Brumfield et al. | 422/46 |
| 3,794,468 | 2/1974 | Leonard | 422/46 |
| 3,856,475 | 12/1974 | Marx | 422/44 |
| 3,898,045 | 8/1975 | Bowley | 422/44 |
| 3,907,504 | 9/1975 | Hammond et al. | 422/44 |
| 3,927,980 | 12/1975 | Leonard | 422/48 |
| 3,929,414 | 12/1975 | Leonard | 422/41 |
| 3,989,626 | 11/1976 | Bentley et al. | 422/48 |
| 3,998,593 | 12/1976 | Yoshida et al. | 422/48 |
| 4,033,724 | 7/1977 | Tamiya | 422/44 |
| 4,073,622 | 2/1978 | Luppi | 422/46 |
| 4,127,111 | 11/1978 | Drolet | 128/2 G |

(List continued on next page.)

FOREIGN PATENT DOCUMENTS

| | | |
|---|---|---|
| 0187708 | 7/1986 | European Pat. Off. . |
| 187708B1 | 8/1992 | European Pat. Off. . |
| 2343845 | 3/1974 | Germany . |
| 528931 | 12/1976 | U.S.S.R. . |
| 279896 | 5/1977 | U.S.S.R. . |
| 256169 | 5/1977 | U.S.S.R. . |
| 819861 | 9/1959 | United Kingdom . |
| 1437493 | 5/1976 | United Kingdom . |

*Primary Examiner*—Nina Bhat
*Attorney, Agent, or Firm*—Barbara A. Wrigley

[57] ABSTRACT

A combination heat exchanger and oxygenator device is provided. The device includes a generally cylindrical housing having first and second compartments with hollow heat exchange tubes and hollow gas exchange tubes disposed therein, a blood inlet, a blood outlet, a heat exchanges medium inlet, a heat exchange medium outlet, an oxygenating fluid inlet and an oxygenating fluid outlet. The housing has a central axis with the second compartment being concentric thereto. The blood flow passage is defined by blood entering the device generally axially through a path extending along the central axis of the housing and flows generally radially through the second, oxygenating compartment.

15 Claims, 3 Drawing Sheets

U.S. PATENT DOCUMENTS

| | | | |
|---|---|---|---|
| 4,138,288 | 2/1979 | Lewin | 128/DIG. 3 |
| 4,138,464 | 2/1979 | Lewin | 422/46 |
| 4,151,088 | 4/1979 | Wolf, Jr. et al. | 210/180 |
| 4,160,801 | 7/1979 | Badolato et al. | 422/46 |
| 4,179,364 | 12/1979 | Bratten et al. | 410/321 B |
| 4,182,739 | 1/1980 | Curtis | 422/47 |
| 4,183,961 | 1/1980 | Curtis | 424/366 |
| 4,196,075 | 4/1980 | Bentley | 210/19 |
| 4,197,876 | 4/1980 | Lobdell | 137/625.47 |
| 4,228,125 | 10/1980 | Lobdell et al. | 422/46 |
| 4,237,091 | 12/1980 | Lobdell | 422/46 |
| 4,261,951 | 4/1981 | Miley | 422/46 |
| 4,268,476 | 5/1981 | Raible | 422/46 |
| 4,297,318 | 10/1981 | Raible | 422/46 |
| 4,315,819 | 2/1982 | King et al. | 210/231.3 |
| 4,336,224 | 6/1982 | Siposs | 422/46 |
| 4,371,122 | 2/1983 | Schuller | 242/43 R |
| 4,374,088 | 2/1983 | Stenberg | 422/46 |
| 4,394,986 | 7/1983 | Hasegawa et al. | 242/1 X |
| 4,396,584 | 8/1983 | Burgess et al. | 422/310 |
| 4,407,777 | 10/1983 | Wilkinson et al. | 422/46 |
| 4,424,190 | 1/1984 | Mather III et al. | 422/46 |
| 4,430,219 | 2/1984 | Kuzumoto et al. | 210/321.3 |
| 4,451,562 | 5/1984 | Elgas et al. | 435/2 |
| 4,469,659 | 9/1984 | Carson et al. | 422/46 |
| 4,490,331 | 12/1984 | Steg, Jr. | 422/46 |
| 4,572,446 | 2/1986 | Leonard et al. | 210/247 |
| 4,620,965 | 11/1986 | Fukusawa et al. | 422/46 |
| 4,639,353 | 1/1987 | Takemura et al. | 422/46 |
| 4,690,758 | 9/1987 | Leonard et al. | 422/46 |
| 4,698,207 | 10/1987 | Bringham et al. | 422/46 |
| 4,715,953 | 12/1987 | Leonard | 422/46 |
| 4,749,551 | 6/1988 | Borgione . | |
| 4,770,852 | 9/1988 | Takahara et al. | 422/48 |
| 4,791,054 | 12/1988 | Hamada et al. | 435/2 |
| 4,808,378 | 2/1989 | Nakanishi | 422/46 |
| 4,818,490 | 4/1989 | Carson et al. | 422/46 |
| 4,902,416 | 2/1990 | Schroeder et al. | 210/321.67 |
| 4,902,476 | 2/1990 | Gordon et al. | 422/46 |
| 4,906,581 | 3/1990 | Baker . | |
| 4,952,312 | 8/1990 | Zantonelli et al. | 210/321.74 |
| 4,971,836 | 11/1990 | Fukasawa et al. | 427/235 |
| 4,975,247 | 12/1990 | Badolato et al. | 422/48 |
| 5,026,479 | 6/1991 | Bikson | 210/321.8 |
| 5,033,686 | 7/1991 | Rebsamen | 242/35.5 R |
| 5,043,140 | 8/1991 | Combs | 422/46 |
| 5,137,531 | 8/1992 | Lee et al. | 422/46 |
| 5,139,741 | 8/1992 | Hagiwara | 422/48 |
| 5,162,101 | 11/1992 | Cosentino et al. | 422/46 |
| 5,188,801 | 2/1993 | Fini | 422/48 |
| 5,217,689 | 6/1993 | Raible | 422/46 |
| 5,230,862 | 7/1993 | Berry . | |
| 5,240,677 | 8/1993 | Jones et al. . | |
| 5,270,004 | 12/1993 | Cosentino | 422/46 |
| 5,346,621 | 9/1994 | Haworth et al. . | |
| 5,376,334 | 12/1994 | Haworth et al. . | | ns. 5,578,267

CYLINDRICAL BLOOD HEATER/OXYGENATOR

This is a continuation of application Ser. No. 08/263,817, filed on Jun. 22, 1994, now abandoned which is a divisional of application Ser. No. 08/115,996, filed on Sep. 2, 1993, now abandoned, which is a continuation of application Ser. No. 07/844,620, now U.S. Pat. No. 5,270,004 filed on May 11, 1992, which claims priority to PCT/US89/04314 filed Oct. 1, 1990, the entireties of which are hereby incorporated by reference.

FIELD OF THE INVENTION

This invention relates to a blood oxygenator having an integral heat exchanging unit, the oxygenator being of the outside perfusion type.

BACKGROUND OF THE INVENTION

Blood Oxygenators

In known blood oxygenators, hollow fibers are used as a means to bring blood into contact with oxygen and provide a means for removal of carbon dioxide from the blood. The fibers are typically made of a homogeneous membrane of gas-permeable material such as silicone or of hollow fibers made of a microporous membrane of hydrophobic polymeric material such as polyolefins.

There are two types of hollow fiber blood oxygenators: the inside perfusion type in which blood is passed through the bores of the hollow fibers while oxygen is passed on the outside of the hollow fibers, and the outside perfusion type. Blood oxygenators of the outside perfusion type pass oxygen through the bores of the hollow fibers while blood is flowed past the outside of the hollow fibers.

Examples of inside perfusion type hollow-fiber oxygenators are disclosed in U.S. Pat. Nos. 4,239,729 and 4,749,551.

In blood oxygenators of the outside perfusion type the oxygen can be distributed uniformly through the spaces between adjacent fibers and the blood can be expected to move with better mixing. However, outside perfusion has had the disadvantage of being subject to less than the desired oxygenation of the blood because of regional channeling of the blood as it passes the outsides of the hollow fibers. Blood-side convective mixing is essential for efficient gas transfer in blood oxygenators. Without such mixing, sharply defined boundary layers of fully oxygenated blood develop near the exchange surfaces and the fluxes of oxygen and carbon dioxide tend to be low. Low transport efficiency results in bulky devices with undesirable high blood priming volumes.

Outside perfusion type blood oxygenators are known in which the hollow fibers are in perpendicular orientation to the direction of blood flow so as to produce more mixing of the blood as the blood flows than inside perfusion constructions. This arrangement can bring about an improvement in oxygenation rate. However, if the number of fibers used in such a blood oxygenator is large (as is desirable) and/or the flow rate of blood is increased in order to treat large volumes of blood, problems arise. For example, unacceptable pressure drop of the blood between inlet and outlets and/or channeling of the blood between groups of fibers may occur. By channeling it is to be understood that a significant flow of blood takes place through relatively large area voids between fibers so that there is little or no mixing. As the rate of oxygen transfer primarily takes place in a thin boundary layer adjacent the hollow fibers, the effectiveness of desired oxygenation is reduced.

Examples of blood oxygenators of the outside perfusion type are disclosed in copending application PCT/US89/00146 filed Jan. 13, 1989; WO 89/00864; and U.S. Pat. Nos. 3,794,468; 4,352,736: 4,622,206; 4,659,549; 4,639,353; 4,620,965; 4,791,054; and 4,808,378, all incorporated herein by reference.

Combined Oxygenator and Heat Exchanger Devices

In the prior art it has been recognized that there is considerable heat loss in all extracorporeal circuits and various devices have been introduced for the purpose of maintaining the temperature of blood within the normal physiological range. Devices which combine the function of blood heating and oxygenation are known. U.S. Pat. No. 4,111,659 describes an embossed film membrane heater/oxygenator. U.S. Pat. No. 4,138,288 describes a bubble-type oxygenator with an integral heater at the blood outlet side of the oxygenator. U.S. Pat. No. 4,620,965 describes an outside perfusion type hollow fiber blood oxygenator with an associated heat exchanger, also located on the blood outlet side of the device, in which the blood flows longitudinally through the oxygenator portion of the device and generally parallel to the hollow gas exchange fibers. U.S. Pat. Nos. 4,639,353, 4,659,549 and 4,791,054 also disclose outside perfusion type hollow-fiber oxygenators in which blood flowing longitudinally through a generally rectangular or cylindrical device passes through multiple hollow fiber exchange chambers separated by narrow channel baffles. In some embodiments of the latter devices, separate heat and Oxygen exchange chambers are provided.

U.S. Pat. No. 4,645,645 describes a hollow-fiber blood oxygenator to which a helical heat exchanger may be attached. Heat exchange is accomplished by passing blood across the outside of a helical coated metal coil.

U.S. Pat. No. 4,424,190 describes another form of hollow-fiber oxygenator with an attached heater compartment displaced longitudinally on a generally cylindrical device.

A problem with prior blood oxygenator/heater combination devices which has been recognized in the prior art is the considerable bulk, with consequent large priming volume of the combined devices. A flat device is described in WO 89/00864 and co-pending application, PCT/US89/00146 filed Jan. 13, 1989, which locates heated exchange fibers and gas exchange fibers in adjacent compartments separated by a porous wall so as to eliminate collection and distribution manifolds between the devices. Such flat devices, however, are difficult to manufacture because of the difficulty of properly packing the gas exchange fibers for optimal efficiency.

SUMMARY OF THE INVENTION

The present invention pertains to a novel compact integrated blood heater/oxygenator in which the blood advantageously flows transversely to the axial direction of hollow heat exchange and oxygenation fibers, the device having a minimal priming volume and which is easily assembled using conventional fiber winding techniques for packing the gas exchange fibers.

The inventive blood heater oxygenator is a generally cylindrical device which is constructed so that the blood enters a central chamber extending longitudinally along the axis of the device and then moves radially through respective annular hollow heat exchange and oxygenation fiber bundles in a direction generally perpendicular to the axis of the device and generally transverse to the axial direction of the fibers toward the outer wall of the device where the temperature adjusted and oxygenated blood is collected and passed out of the device via an exit port.

DESCRIPTION OF THE PREFERRED EMBODIMENT

Figure 1:
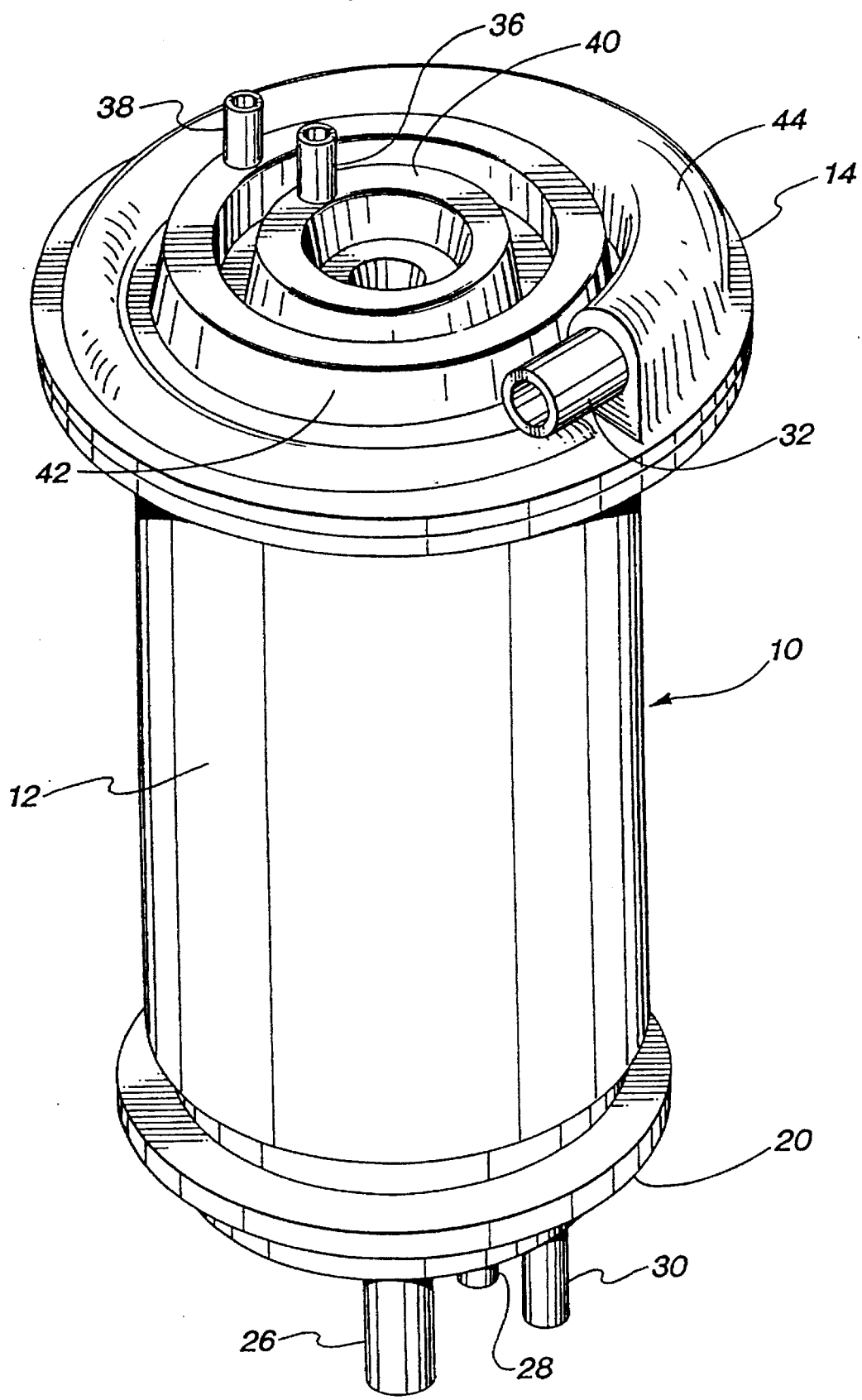
FIG. 1 is a side perspective view of a blood heat exchanger/oxygenator of the invention.

The invention is best described by reference to the preferred embodiment as illustrated in FIGS. 1–5.

The preferred heat exchanger/oxygenator device of the invention is generally designated in the figures by the numeral 10. The exterior of device 10 comprises a generally cylindrical exterior wall portion 12, proximal cover member 14 and distal cover member 20. The distal cover 20 includes a central blood inlet port 26, a heating fluid outlet port 28 and a gas outlet port 30.

The proximal cap 14 includes a blood outlet port 32, a heater exchange fluid inlet port 36 and a gas inlet port 38. Raised circular portions 40 and 42 define heat exchange fluid and gas distribution manifolds, respectively, which provide fluid communication between the respective inlet ports 36 and 38 and respective hollow bundles of heat exchange and gas exchange fibers, respectively, within the device. A raised circular portion 44 defines a blood collecting manifold which, as shown in FIG. 1, increases in dimension as it approaches the exit port 32.

On the distal cover 16 there are also included raised circular portions 46 and 48 which define manifolds for collecting and directing heat exchange fluid and oxygenation gas from the fiber bundles to their respective outlet ports.

The interior of the device includes a series of annular cylindrical chambers 50, 54, 58 and 62 separated by tubular porous wall members 52, 56 and 60.

The central chamber 50 communicates with blood inlet port 26. The next outward annular chamber 54 comprises the heat exchanger portion of the device and is filled with heat exchange tubes 70 of known type which extend generally in an axial direction. Annular chamber 58 comprises the oxygenator portion of the device and is filled with tubes 74 of a gas exchange membrane material, also of known type. The gas exchange tubes 74 are also preferably oriented generally in an axial direction. Between the porous wall 60 and the inner surface of the outer wall 12 of the device is a hollow cylindrical blood collection chamber 62.

The tubular porous walls 52, 56, 60, the heat exchange tubes 70, and gas exchange tubes 74 are all potted together with a conventional potting material 76 which holds the various interior components of the device together as a unit and isolates the open ends of the tubes 70 and 74 from the blood flow path.

Figure 2:
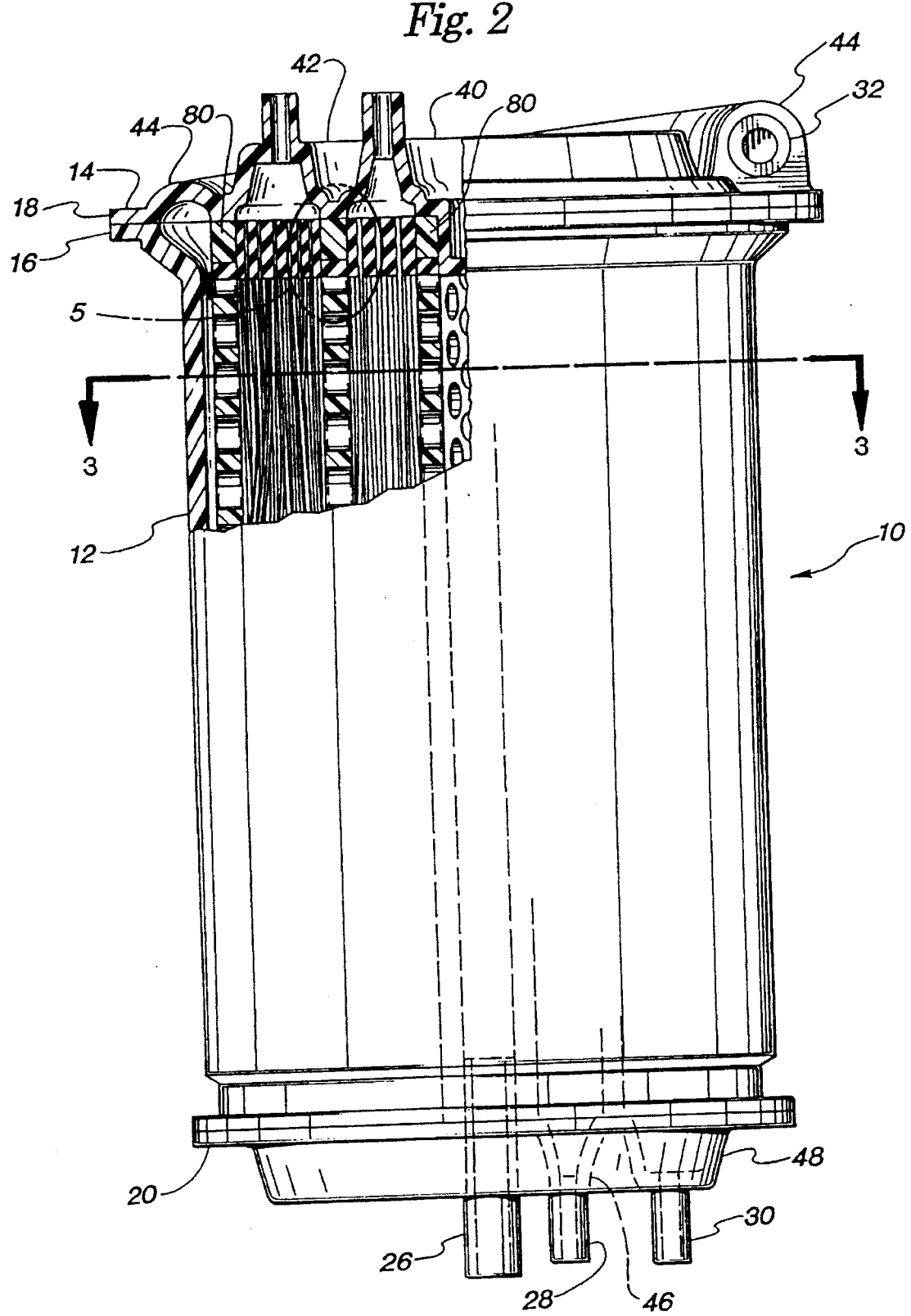
FIG. 2 is a side plan view with parts cut away of the heat exchanger/oxygenator of FIG. 1.
Figure 3:
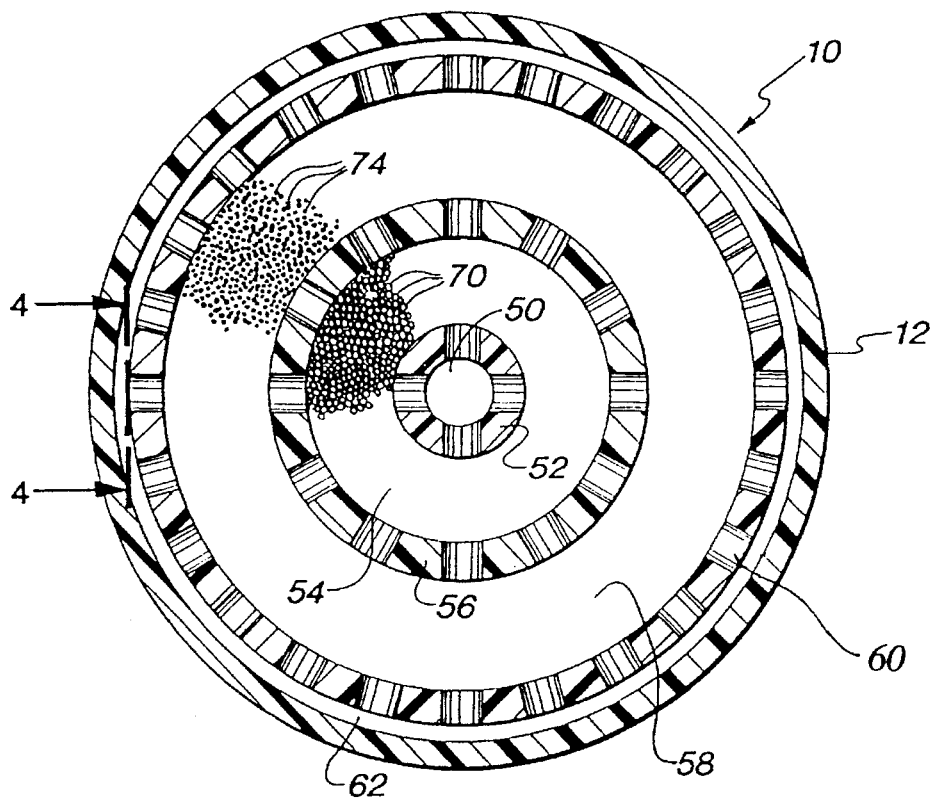
FIG. 3 shows a sectional view of the heat exchanger/oxygenator of the invention taken along line 3—3 of FIG. 2.
Figure 4:
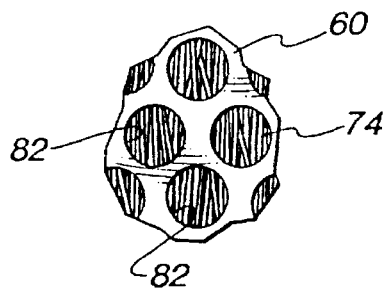
FIG. 4 is a side view of a portion of the device as seen from line 4—4 of FIG. 3.
Figure 5:
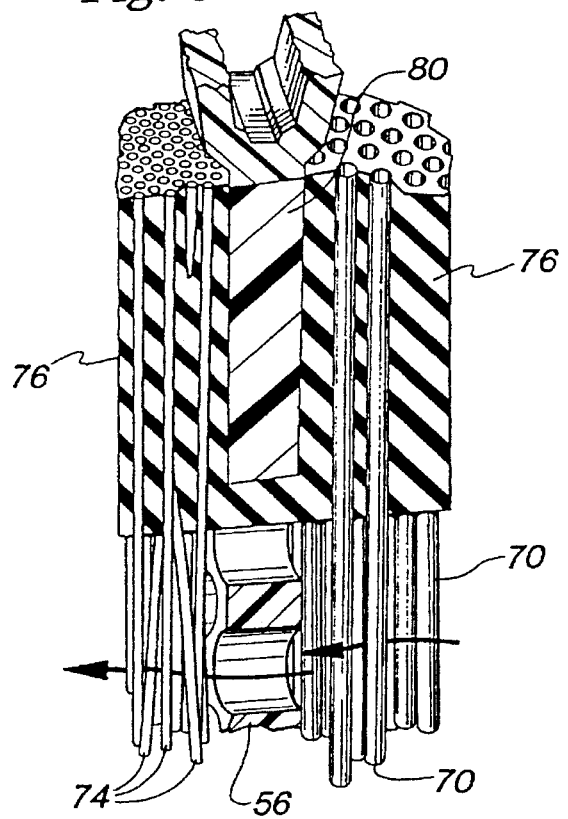
FIG. 5 is an enlarged perspective view of the portion of FIG. 2 indicated by the bold numeral 5.

The respective bundles of heat exchange and gas exchange fibers are desirably simultaneously end potted so as to produce a unitary assembly which can be readily sheared to produce open tube ends as best shown in FIG. 5. The covers 14 and 16 are aligned so that they sealingly engage the potted assembly between the respective fiber bundles. Suitably the porous tubular wall members 52, 56 and 60 are provided with continuous non-porous end portions 80 entrained in the potting material such that when the potted assembly is sheared the end portions 80 expose continuous annular rings which provide sealing surface to engage the covers and isolate the respective gas blood and heating fluid distribution and collection manifolds, as shown in FIGS. 2 and 5. Most preferably the cover assemblies are heat or sonically welded to the end portions 80 and to the ends of outer cylindrical wall 12.

The tubular porous wall members 52, 56 and 60 provide separation between the chambers while allowing blood to pass therethrough without offering substantial resistance or directional change. Any porous structure which allows the passage of blood without significant damage may be used. However, it is preferred that these wall members be constructed of a biocompatible plastic material containing a plurality of spaced orifices 82. The orifices 82 are preferably no greater than ½ inch (1.27 cm) and preferably ⅜ inches (0.95 cm) in diameter. Larger diameter orifices will allow the fibers to bulge into the orifices and thereby potentially create void spots in the fiber bundle therebelow. Another disadvantage in fibers bulging into the orifices is that pinching to close a fiber may occur. Smaller diameter orifices may be used, but spacing must be selected so that the total area of the orifices 82 is sufficient to assure that the respective porous tubular wall members do not themselves create significant resistance to blood flow or dead spots where blood may collect and coagulate.

Suitable gas exchange membrane material for fibers 74 may be made of polypropylene, polyethylene or other biocompatible material which provides gas exchange. The fibers are liquid impermeable. Suitable fibers for this purpose are well known and commercially available from a number of manufacturers including Mitsubishi Rayon Sale, Ltd. of Tokyo, Japan and Celanese Chemical Company of New York, N.Y., U.S.A.

The heat exchange tubes 70 are preferably formed from a polyurethane resin such as B. F. Goodrich Estane 58091. The tubes are much larger than the hollow fibers in the oxygenator, typically being about 0.033 inches (840 microns) in outside diameter with a wall thickness of about 0.004 inches (102 microns). In contrast, a typical oxygenator fiber has an outside diameter of about 200–450 microns and a wall thickness of less than 50 microns. The formation of heat exchanger tubes from polyurethane rather than the stainless steel, polyethylene, or polypropylene is preferred. While the efficiency of the heat exchange it an important design consideration, it is vital that there must be no leakage. The end seals where polyurethane potting compounds are used with stainless steel tubes represent potential leakage areas of the cooling fluid into the blood.

The use of polyurethane heat exchange tubes with the polyurethane end potting compounds provides a positive seal which ensures that no leakage will occur. This compatibility with the potting compound greatly increases the safety of the product.

The hollow heat exchange tubes are packed into chamber 70 such that channeling is minimized. However, performance of the heat exchanger is not greatly affected if some channeling is present. A pack density of between about 40% and 60% provides an efficient heat exchanger with an accept&hie pressure drop. It is preferred to pack the polyurethane tubes at about 45%–55% pack density which provides an efficient unit, low pressure drop and low blood priming volume. The thin walled polyurethane hollow tubes provide good heat transfer. The efficiency desired is in ensuring that all of the blood is heated or cooled as desired, not in how much heat exchange fluid is required. The temperature differential between the blood and heat exchange fluid should be low to provide better control.

In the preferred embodiment the overall size of the unit is approximately 5 inches (12.5 cm) in diameter by 7.5 inches (18.75 cm) long. The heat exchange tubes are polymeric tubes having an approximate diameter of 0.033 inches (0.83 mm or 830 μ), and the heat exchange chamber containing approximately 2750 tubes. The gas exchange fibers suitably are microporous hollow polypropylene membrane is sufficient quantity to provide a total blood contact surface area of approximately 3.8 square meters. The device permits an outlet blood oxygen tension of 150 torr or more, tested on bovine blood with a hemoglobin concentration of 12 gram-percent; with an inlet saturation of 55% a blood flow of 6 liters per minute and an oxygen flow of 6 liters per minute. The heat exchanger provides an effectiveness level of 45% as measured by the protocol of the American Association of Medical Instrumentation (AAMI).

The heat exchange tubes are preferably cut to length and then placed into the chamber 52. Winding the tubes about central core 52 is less preferable as it tends to cause the hollow tubes to bend and may cause cracks or breaks.

The gas exchange fiber bundle is most suitably prepared by spiral winding fibers 74 around the tubular wall member 56, successive layers being angled relative to each other to produce a crisscross pattern. The crossing fiber arrangement is preferred over parallel fiber packing since it forces the blood into effective but gentle transverse, mixing without traumatizing the blood. Winding techniques for producing cylindrical bundles of hollow fibers are well known and are described in such references as U.S. Pat. No. 3,755,034, 3,794,468, 4,224,094, 4,336,138, 4,368,124 and 4,430,219, all incorporated herein by reference. The preferred angle between the fibers of successive layers is in the range of between about 10° and 30°, more preferably between about 15° and 20°, most preferably 18°. The fibers run in a generally axial direction, so that an axial plane bisects the angle between the successive layers of the fibers. For instance, in the most preferred embodiment, one layer will deviate from the axial direction by +9° and the next layer will deviate from the axial direction by −9°. The pack density of the gas exchange fibers 74 should be between about 45% and 60%, most preferably about 50% and 55%. When the pack density is too high the resulting resistance to blood flow reduces oxygenation efficiency. Likewise, when the pack density is too low channeling and reduced turbulent flow of the blood also reduces oxygenation efficiency. Within the preferred range oxygenation efficiency is maximized.

For potting the ends of the assembly of fiber bundles and porous wall members 52, 56 and 60, a polyurethane potting compound is preferred. Suitable potting compounds are available from Caschem, Inc. of Bayonne, N.J., U.S.A. A polyurethane casting system of Caschem, Inc. is described in U.S. Pat. Reissue No. 31,389. After potting the hollow fibers are reopened by conventional techniques such as shearing the potting with a sharp knife so as to expose the interiors of the fibers.

After insertion of the potted and sheared assembly into cylinder 12 the cover members 14 and 20 are inserted in line so that they sealingly engage the potted assembly between the respective fiber bundles.

The covers 14 and 20, cylinder case 12 and the porous tubular wall members 52, 56 and 60 are all preferably made from nontoxic biocompatible plastic resins. Suitable resins are polycarbonate resins such as the Lexan brand resins of General Electric Company, Polymer Product Department, Pittsfield, Mass. Lexan 144 grade polycarbonate resins are currently preferred.

In operation, blood entering the device through the central inlet port 26, fills chamber 50 and then passes in a direction generally perpendicular to the axis through porous wall 52, around heat exchange fibers 70, through porous wall 56, around gas exchange fibers 74, through wall 60, into collection chamber 62 and then up into the blood collecting manifold 44 in cover 14, finally exiting the device via blood exit port 32.

An advantage provided by the compact structure of the device is a reduction in priming volume which results because blood is directly passed from the heat exchange chamber 54 to the oxygenation chamber 58 without passing through intermediate collection and distribution manifolds.

Yet another advantage of the invention compared to many of the prior art devices described in the Background section, above, is the location of the heat exchange chamber upstream from the gas exchange chamber. Since gas solubility varies significantly with temperature, it is important that the blood is oxygenated at the temperature it will enter the body. If the blood is heated after it is oxygenated, the oxygenation level may exceed the gas saturation point at the higher temperature, resulting in formation of dangerous emboli. If blood is cooled after oxygenation inefficient oxygenation can result.

Compared to the rectangular devices of WO 89/0864 and PCT/US89/00146, the device of the present invention also provides a significantly less complicated device to manufacture. In particular, to obtain the desired angular and Offset orientation of the gas exchange fibers in the prior art rectangular device it was necessary to employ a manufacturing technique which not only laid alternate layers in a crisscross pattern angled with respect to each other approximately 18', but also required offsetting each successive parallel layer to minimize channeling. In the cylindrical device of the invention the desired crisscrossing of successive layers can readily be performed by conventional spiral winding techniques and the increasing diameter of the winding naturally results in an offset of successive parallel layers without complex controls.

What is claimed is:

1. A combination heat exchanger and oxygenator device comprising:

a housing including structure defining first and second compartments, a blood inlet, a blood outlet, a heat exchange medium inlet, a heat exchange medium outlet, an oxygenating fluid inlet and an oxygenating fluid outlet, said housing having a central axis, said second compartment being concentric to said axis;

structure defining a flow passage for blood through said housing from said blood inlet to said blood outlet;

structure defining a flow passage for heat exchange medium from said heat exchange medium inlet to said heat exchange medium outlet;

structure defining a flow passage for oxygenating fluid from said oxygenating fluid inlet to said oxygenating fluid outlet;

a plurality of hollow gas exchange tubes disposed in said second compartment;

said blood flow passage comprising a heat exchange path through said first compartment, said blood flow passage further comprising a central path extending along at least a portion of said central axis of said housing, said blood flow passage further comprising an oxygenating path extending generally radially through said second compartment, around said gas exchange tubes, said central path being upstream of said oxygenating path, whereby blood flows axially along at least a portion of the central axis of said housing and then generally radially through said second compartment.

2. The combination heat exchanger and oxygenator device of claim 1, wherein said blood outlet has a central fluid flow axis disposed in a plane substantially transverse to said central axis of said housing.

3. The combination heat exchanger and oxygenator device of claim 1, wherein said oxygenating fluid inlet and oxygenating fluid outlet respectively comprise a gas inlet and a gas outlet.

4. The combination heat exchanger and oxygenator device of claim 1, wherein said heat exchange path extends generally radially through said first compartment.

5. The combination heat exchanger and oxygenator device of claim 1, wherein said central path is upstream of said heat exchange path.

6. The combination heat exchanger and oxygenator device of claim 1, wherein said heat exchange path is upstream of said oxygenating path.

7. The combination heat exchanger and oxygenator device of claim 1, wherein said first and second compartments are concentric.

8. The combination heat exchanger and oxygenator device of claim 1 wherein said plurality of hollow gas exchange tubes disposed in said second compartment are comprised of hollow gas exchange tubes generally longitudinally disposed within said first compartment.

9. The combination heat exchanger and oxygenator device of claim 1 wherein said plurality of hollow gas exchange tubes disposed in said second compartment are comprised of hollow gas exchange tubes that are spirally wound in concentric layers extending generally longitudinally.

10. The combination heat exchanger and oxygenator device of claim 1 wherein said first compartment is upstream of said second compartment.

11. The combination heat exchanger and oxygenator device of claim 1 wherein said structure defining a flow passage for heat exchange medium from said heat exchange medium inlet to said heat exchange medium outlet includes a plurality of hollow heat exchange tubes disposed in said first compartment.

12. The combination heat exchanger and oxygenator device of claim 11, wherein said heat exchange path is defined around said heat exchange tubes and said heat exchange medium flows through said heat exchange tubes.

13. The combination heat exchanger and oxygenator device of claim 11, wherein said blood flow passage extends axially of said first compartment, via said central path, and then radially through said first compartment, around said heat exchange tubes, via said heat exchange path, and then radially through said second compartment, around said gas exchange tubes, via said oxygenating path.

14. The combination heat exchanger and oxygenator device of claim 11 wherein said plurality of hollow heat exchange tubes disposed in said first compartment are comprised of heat exchange tubes generally longitudinally disposed within said first compartment.

15. The combination heat exchanger and oxygenator device of claim 1, wherein said blood flow passage extends axially of said first compartment, via said central path, and then radially through said first compartment, via said heat exchange path, and then radially through said second compartment, via said oxygenating path.

* * * * *